US006887499B2

(12) United States Patent
Bababunmi

(10) Patent No.: US 6,887,499 B2
(45) Date of Patent: *May 3, 2005

(54) FORMULATION AND METHOD FOR TREATING SKELETAL MUSCLE DEGENERATION CAUSED BY MALNUTRITION AND DISEASE

(76) Inventor: Enitan A. Bababunmi, 5554 Cobb Meadow, Norcross, GA (US) 30093

( * ) Notice: Subject to any disclaimer, the term of this patent is extended or adjusted under 35 U.S.C. 154(b) by 153 days.

This patent is subject to a terminal disclaimer.

(21) Appl. No.: 10/252,525

(22) Filed: Sep. 24, 2002

(65) Prior Publication Data

US 2003/0021858 A1 Jan. 30, 2003

Related U.S. Application Data

(63) Continuation-in-part of application No. 09/863,069, filed on May 22, 2001, now Pat. No. 6,465,021.
(60) Provisional application No. 60/205,551, filed on May 22, 2000.

(51) Int. Cl.$^7$ .............................................. A61K 35/78
(52) U.S. Cl. ........................ 424/757; 424/725; 426/629; 426/590; 514/27; 514/456
(58) Field of Search ................................. 424/725, 757; 426/629, 590; 514/27, 456

(56) References Cited

U.S. PATENT DOCUMENTS 6,465,021 B2 * 10/2002 Bababunmi ................. 424/757
2003/0096375 A1 * 5/2003 Smith et al. .................. 435/84

* cited by examiner

Primary Examiner—Leon B. Lankford, Jr
Assistant Examiner—Ruth A. Davis
(74) Attorney, Agent, or Firm—Edell, Shapiro & Finnan, LLC

(57) ABSTRACT

A formulation is provided for the treatment of the adverse affects of skeletal muscle degenerative diseases prevalent in humans in developing countries. The formulation typically includes a first component including at least one of jasmone, a jasmonate, jasmonic acid, oxo-phytodienoic acid, and a second component including at least one of an antioxidant and carnitine. Additionally, soy milk may be utilized as a delivery vehicle for the formulation for oral ingestion by a subject. The formulation is designed to replenish energy levels in disease infected muscle cells, reinstate calcium homeostasis within the muscle cells, and reduce the activity of oxidizing free radical reactions typically caused by muscle degenerative diseases.

22 Claims, No Drawings

FORMULATION AND METHOD FOR TREATING SKELETAL MUSCLE DEGENERATION CAUSED BY MALNUTRITION AND DISEASE

CROSS REFERENCE TO RELATED APPLICATIONS

This application is a continuation-in-part of U.S. patent application Ser. No. 09/863,069, entitled "Formulation and Method For Treating Skeletal Muscle Degeneration Caused By Malnutrition and Disease", and filed May 22, 2001, now U.S. Pat. No. 6,465,021 issued Sep. 15, 2002, which claims priority from U.S. Provisional Patent Application Ser. No. 60/205,551, entitled "Formulation and Method For Treating Human Skeletal Muscle Degenerative Diseases", and filed May 22, 2000. The disclosures in the above-referenced patent applications are incorporated herein by reference in their entireties.

BACKGROUND OF THE INVENTION

1. Technical Field

The present invention relates to formulations for counteracting skeletal muscle cell damage and degeneration due to the effects of malnutrition and various muscle degenerative diseases.

2. Description of the Problem

The devastating effect of malnutrition on worldwide child mortality rates has been well documented. Indeed, statistical studies of worldwide mortality data indicates that approximately 70% of the millions of deaths occurring annually among children less than 5 years old in developing countries is associated with malnutrition singly, or in combination with diseases such as malaria, diarrhea, measles, or acute respiratory infections. Two forms of malnutrition prevalent in developing African and Asian countries are kwashiorkor and marasmus. Both are forms of protein-energy malnutrition characterized by growth retardation in children and wasting of subcutaneous fat and muscle. Many factors add to and promote the deleterious effects of malnutrition including ingestion of toxins and viral infection.

Chronic ingestion of fungal mycotoxins by humans, particularly cyclopiazonic acid (CPA) and aflatoxin (AFL), contribute significantly to the development of malnutrition and liver cancer, respectively. CPA, an indolic fungal metabolite, coexists with AFL, a liver carcinogen, in nature. Assays of both CPA and AFL indicate that the two mycotoxins elicit their toxic effects by independent modes of action. The mechanism of the toxicity of CPA in mammals and its role as a very common toxic food contaminant is now well established. CPA is a specific inhibitor of Ca-ATPase in the skeletal muscle (sarcoplasmic reticulum) of mammals. See Goeger et al., *Biochemical Pharmacology*, 37, 978–981 (1988). Ca-ATPase controls the pumping of calcium within the sarcoplasmic reticulum to effect muscle contraction or relaxation. Inhibition of Ca-ATPase by CPA prevents the pumping of calcium in the muscle cell that would otherwise be used for maintaining overall health of the cell, thus resulting in a wasting and degeneration of muscle cell tissue.

Apoptosis has also been found to occur in skeletal muscle in response to CPA-induced cell damage caused by perturbation of Ca-homeostasis and Ca-ATPase. Apoptosis is an active form of cellular death and constitutes a strictly regulated device for the removal of damaged cells. Apoptosis plays a very important physiological role during organ development and is involved in disease pathogenesis. Enhanced apoptosis of cells participates in chronic pathologies such as in muscle degenerative diseases. For example, an apoptotic phenomenon exists in the skeletal muscle of experimental models of cancer cachexia, using the rat Yoshida AH-130 ascites hepatoma (liver tumor). See van Royen et al., *Biochem Biophys Res Commun*, 270(2): 533–537 (Apr. 13, 2000).

Another muscular-degenerative disease is hepatocellular carcinoma (HCC), which accounts for 80–90% of all liver cancers worldwide. HCC is also one of the ten most frequent cancers worldwide, accounting for 4% of the total. Major contributory factors of HCC are presumed to be fungal toxins found in foods, such as the previously noted CPA and AFL. The incidence of HCC is prevalent in men in African and Asian countries, infecting 4 out of every 10,000 people. There has been a strong indication that mycotoxins acting in concert with other factors such as malnutrition, infectious diseases and the hepatitis B virus (HBV) could be responsible for the high incidence of HCC in Africa and Asia.

HIV also causes a form of virus-induced skeletal muscle degenerative disease, namely, AIDS. Malnutrition is common among individuals suffering from advanced HIV-disease. HIV/AIDS malnutrition has a major influence on the progression of the disease. Therefore, early and ongoing nutritional and pharmacological interventions that modify and/or control the dietary intake of a subject having HIV/AIDS can minimize the progression of the disease. In fact, nutritional supplementation of HIV/AIDS patients is necessary because it might lead to improved immune function. Additionally, dietary supplements with antioxidants (e.g., vitamins C and E) at supranutritional doses have been found to protect against oxidative damage to skeletal muscle mitochondria caused by the antiretroviral agent AZT.

Many different classes of chemicals affect Ca-homeostasis adversely. Several of these compounds also adversely affect the redox state of cells causing oxidative stress. It would therefore be advantageous to develop a pharmaceutical agent or formulation that counteracts the negative effects of skeletal muscle degenerative diseases without adversely affecting calcium levels or the redox state of the muscle cells.

SUMMARY OF THE INVENTION

Therefore, in light of the above, and for other reasons that become apparent when the invention is fully described, an object of the present invention is to provide a formulation for preventing the degeneration of skeletal muscle tissue commonly caused by malnutrition and degenerative diseases such HCC and AIDS.

Another object of the present invention is to provide a formulation for preventing the degeneration of skeletal muscle tissue that does not adversely affect Ca-homeostasis or induce additional oxidative stress of the muscle cells.

A further object of the present invention is to provide a method of delivering a formulation for preventing the degeneration of skeletal muscle tissue in subjects in an easy, efficient and substantially non-intrusive manner.

The aforesaid objects are achieved individually and in combination, and it is not intended that the present invention be construed as requiring two or more of the objects to be combined unless expressly required by the claims attached hereto.

In accordance with the present invention, a formulation comprising at least one of jasmone, jasmonate, jasmonic acid and oxo-phytodienoic acid is administered to a subject in an effective amount to prevent the degeneration of skeletal muscle tissue. The formulation may also include at least one of an antioxidant and carnitine provided in effective amounts to further prevent the degeneration of skeletal muscle tissues. The antioxidant preferably includes a phytoestrogen. Most preferably, the phytoestrogen includes an isoflavone such as genistein or daidzein. The formulation may further include soy milk as a delivery vehicle for oral ingestion by the subject.

The above and still further objects, features and advantages of the present invention will become apparent upon consideration of the following detailed description. While the detailed description discloses specific details of the invention, it should be understood that variations may exist and would be apparent to those skilled in the art.

DESCRIPTION OF THE PREFERRED EMBODIMENTS

According to the present invention, a novel formulation is described herein which prevents the degeneration of skeletal muscle tissue caused by malnutrition and other degenerative diseases such as HCC and AIDS. As previously noted, certain mycotoxins, such as CPA and AFL, play a major role in protein-energy malnutrition and the degeneration of skeletal muscle tissue. These mycotoxins are typically orally ingested via fungi-contaminated foods and are the cause of reduced Ca-ATPase activity in the muscle sarcoplasmic reticulum (SR).

Erythrocyte calcium-pumping activity and xenobiochemical studies in protein-energy malnutrition have received a great deal of attention over the last several years. See, for example, Okunade et al., Bioscience Reports, 9, 359–68 (1984) and Thabrew et al., Xenobiotica, 12, 849–853 (1982). Studies such as these have led to the conclusion that reduced Ca-ATPase activity in protein-energy malnutrition may be linked with the generation of reactive oxygen species. Furthermore, damage to skeletal muscle by different stresses has been found to occur by three common pathways or reactions (McArdle et al., Basic and Applied Myology, 4, 43–50 (1981)):

(i) Loss of energy supply to the cell;

(ii) Loss of intracellular calcium homeostasis; and (iii) Over-activity of oxidizing free radical reactions.

Therefore, apart from inhibiting muscle SR Ca-ATPase activity, CPA and AFL also induce oxidative stress and cell damage as well as deplete cell energy. As described herein, the formulation of the present invention will counteract the negative effects caused by mycotoxins by specifically addressing the three reactions associated with muscle stress and damage.

The formulation of the present invention typically comprises an effective amount of at least one member of the jasmonate family. As used herein, the term "jasmonate family" refers to cyclopentanones and cyclopentenones including jasmone, jasmonates such as methyl jasmonate, jasmonic acid and oxo-phytodienoic acid (OPDA). In addition, the term "effective amount" refers to an amount of a particular component in the formulation that renders the formulation effective in preventing the degeneration of skeletal muscle tissue. Any one or combination of these members of the jasmonate family is believed to be essential in the formulation of the present invention to combat the inhibition of Ca-ATPase and re-establish intracellular calcium homeostasis.

Jasmone is a natural methylpentylcyclopentenone found primarily in oils extracted from plants such as jasmine flowers. Similarly, methyl jasmonate, jasmonic acid and OPDA are also naturally derived and present in plants and plant oils. Many cyclopentenones, particularly prostaglandins, are used clinically in the treatment of various diseases including cancer. Therefore, there is an indication that jasmone and other cyclopentenones and/or cyclopentanones of the jasmonate family, utilized at non-toxic doses, should be useful in the treatment of muscle degeneration caused by malnutrition and other diseases. Specifically, jasmone, jasmonates, jasmonic acid and OPDA, utilized alone or in any selected combination with each other, are believed to counteract the specific inhibition of Ca-ATPase by mycotoxins such as CPA, thereby positively regulating calcium activity in muscle cells.

While members of the jasmonate family, utilized alone or in combination with each other, are believed to be effective in treating the adverse effects of skeletal muscular degenerative diseases, the formulation may be enhanced via the addition of certain other components. Preferably, the formulation comprises an effective amount of at least one member of the jasmonate family combined with at least one of an antioxidant and carnitine. Most preferably, the formulation will include effective amounts of at least one member of the jasmonate family, carnitine and an antioxidant.

Antioxidants are typically provided in the formulation of the present invention to minimize or prevent muscle wasting induced by oxidative stress. Effective antioxidants suitable for use in the present invention include phytoestrogens, namely isoflavones. Preferably, a soy isoflavone such as genistein, daidzein or combinations thereof will be useful in the formulation of the present invention. Genistein and daidzein each occur naturally and may be isolated from fermented soy products. Each isoflavone has a positive effect in counteracting the oxidative stress to muscle cell tissue that typically occurs in muscle degenerative diseases. In particular, Genistein is a potent antioxidant capable of reversing the deleterious action of CPA. Additionally, Genistein is a specific inhibitor of tyrosine kinase, an extra cellular signal-regulated kinase that is activated by oxidative stress in cells. Daidzein has similar properties as genistein and will also be effective in counteracting reactions induced by mycotoxins leading to muscle damage. The combination of at least one member of the jasmonate family with an antioxidant such as genistein, daidzein or combinations thereof has a synergistic beneficial effect of establishing calcium homeostasis and reduced oxidative stress within disease infected and malnourished muscle cells.

Carnitine, an optional third component of the present invention, is important for restoring energy that has been depleted in muscle cells as a result of protein-energy malnutrition and/or disease. The formulation of the present invention typically includes an effective amount of L-carnitine, which is a naturally occurring L-isomer of carnitine that already exists in human body tissues and plays a crucial role in fat metabolism and energy production. In fact, it is known that L-carnitine plays a critical role in normal skeletal muscle bioenergetics. Specifically, L-carnitine facilitates the control of beta-oxidation of long-chain fatty acids for the restoration of energy that has been lost during muscle damage and degeneration. Therefore, the addition of L-carnitine in the formulation of the present invention effectively maintains adequate energy levels within muscle cells that would otherwise be depleted during muscle degeneration.

The components may be combined (e.g., mixed together, blended, agitated, etc.) in solution for administration to a subject during treatment. Preferably, an effective amount of each desired component is added to a liquid solution for oral ingestion by the subject. Soy milk will provide a useful delivery vehicle for oral ingestion of the formulation due to its widespread use in developing countries such as Africa. Additionally, soy milk provides additional isoflavones that enhances the effect of the formula. However, it is noted that any suitable liquid solution (e.g., cow's milk, water, fruit juice, etc.) may be provided that is capable of dispersing the components of the formulation and preferably has a taste that is desirable for oral ingestion. Additionally, it is noted that the components may be combined in dry form and ingested without the use of a liquid solution.

Although the effective amount of each component may vary based upon the subject being treated, each component will have a suitable activity when provided in the formulation in the following amounts: about 80–240 micrograms of one or more members of the jasmonate family, about 16–24 milligrams of antioxidant and about 2.4–3.6 grams of carnitine. Additionally, the components are typically immersed within an adequate amount, typically about 1 liter, of solution. Most preferably, a formulation of the present invention includes at least 100 micrograms of one or more members of the jasmonate family, at least 20 milligrams of antioxidant and at least 3 grams of carnitine disposed within 1 L of soy milk.

An exemplary method for preparing and administering a formulation according to the present invention is described as follows. One hundred micrograms of at least one member of the jasmonate family (e.g., a pharmaceutically acceptable salt of jasmone and/or methyl jasmonate) may be combined with 20 milligrams of genistein and 3 grams of L-carnitine in 1 L of soy milk. The resultant formulation may be combined in any desirable manner (e.g., hand mixed or mechanically blended or agitated) as desired to provide a suitable dispersion of the components in the milk. Administration of the formulation is achieved by oral ingestion of the entire formulation by a subject. Typically, the subject orally ingests the formulation on a daily basis. The number of days in which the formulation should be ingested depends upon the subject's level of skeletal muscle degeneration and the specific cause of such degeneration (i.e., specific form of malnutrition and disease).

An exemplary method for treating subjects infected with skeletal muscular degenerative diseases is described as follows. At least sixty Nigerian-African human subjects may be studied, wherein each subject is diagnosed with non-cerebral severe falciparum malaria complicated with marasmus and having a similar degree of skeletal muscular degeneration as determined by the measurement of baseline levels of serum creatine kinase (CK) and lactate dehydrogenase (LDH) in each subject. A correlation between muscle damage and increased levels of CK and LDH in muscle tissue has been documented, for example, by Knitter et al., *J Appl Physiol*, 89(4): 1340–1344 (October 2000). At least thirty of the subjects may be placed into a test group, with the remaining subjects being placed into a control group. The test group of subjects may be treated with a daily dosage of the formulation prepared in a substantially similar manner as described above. The formulation will contain about 100 micrograms of at least one member of the jasmonate family (e.g., a pharmaceutically acceptable salt of jasmone and/or methyl jasmonate) combined with 20 milligrams of genistein and 3 grams of L-carnitine, wherein all of the components will be dispersed in about 1 L of soy milk. The formulation may be administered to each patient of the test group on a daily basis for a period of about six weeks, whereas a placebo may be administered to each patient of the control group during the same six week period. Any additional required treatment will be conducted in a substantially similar manner for patients in both groups during the six week clinical trial period. The testing procedures for the six week clinical trial will be carried out in accordance with the Helsinki Declaration of 1975 as revised in 1983 and accepted by the Ethical and Research Committees of Nigerian Federal Ministry of Health National Hospitals and the Schools of Medicine.

After the six week period, assays may be conducted of P-type ion-motive ATPases, including Ca-ATPase, on muscle biopsies of subjects in both the test and control groups to determine differences in muscle tissue health between the two groups. The specific assays may be conducted in accordance with any conventional method for isolating and/or determining concentration of Ca-ATPase concentrations in human tissue. See, for example, Everts et al., *Muscle Nerve*, 15(2): 162–167 (February 1992); Bababunmi et al., *Biochem J.*, 248(1): 297–299 (Nov. 15, 1987); Bababunmi et al., *Int. J. Biochem*, 19(8):721–724 (1987); and Bababunmi et al., *Comp. Biochem. Physiol. B*, 82(1): 117–122 (1985). The results of the assay will indicate a decrease in CK and LDH activity for subjects in the test group in comparison to subjects in the control group, which is indicative of the prevention of further muscle degeneration in the test subjects as a result of the formulation of the present invention.

Thus, the formulations of the present invention are useful in combating the multiple adverse effects of malnutrition and other degenerative diseases on muscle tissue. Specifically, the formulations have the effect of reducing the adverse effects on muscle cells typically caused by inhibition of Ca-ATPase by certain mycotoxins (e.g., CPA and AFL).

The specific embodiments illustrated and described herein are intended to be exemplary and not limiting on the scope of the invention. Having described specific embodiments of novel formulations and corresponding methods for preventing skeletal muscle degeneration caused by malnutrition and disease, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed:

1. A formulation comprising jasmone and carnitine.

2. A formulation comprising a first component selected from the group consisting of a jasmonate, jasmonic acid, oxo-phytodienoic acid and combinations thereof, and a second component comprising carnitine.

3. The formulation of claim 2, wherein the jasmonate includes methyl jasmonate.

4. The formulation of claim 2, wherein the second component further comprises an antioxidant, and the antioxidant comprises an isoflavone.

5. The formulation of claim 4, wherein the antioxidant comprises a soy isoflavone selected from the group consisting of genistein, daidzein and combinations thereof.

6. The formulation of claim 4, wherein the amount of antioxidant in the formulation is in the range of about 16 milligrams to about 24 milligrams.

7. The formulation of claim 2, further comprising soy milk.

8. The formulation of claim 2, wherein the amount of the first component in the formulation is in the range of about 80 micrograms to about 240 micrograms.

9. The formulation of claim 2, wherein the second component includes carnitine in an amount in the range of about 2.4 grams to about 3.6 grams.

10. The formulation of claim 2, wherein the second component further comprises an antioxidant and each of the first component, antioxidant and carnitine is provided in an effective amount in the formulation to prevent degeneration of skeletal muscle tissue of a subject when the formulation is ingested by the subject.

11. The formulation of claim 10, wherein the amount of the first component in the formulation is at least about 100 milligrams, the amount of the antioxidant in the formulation is at least about 20 milligrams and the amount of carnitine in the formulation is at least about 3 grams.

12. A formulation comprising carnitine, an isoflavone selected from the group consisting of genistein, daidzein and combinations thereof, and a jasmonate family component selected from the group consisting of a jasmonate, jasmonic acid, oxo-phytodienoic acid and combinations thereof.

13. The formulation of claim 12, wherein the jasmonate includes methyl jasmonate.

14. The formulation of claim 12, wherein each of the carnitine, isoflavone and jasmonate family component is provided in an effective amount in the formulation to prevent degeneration of skeletal muscle tissue of a subject when the formulation is ingested by the subject.

15. The formulation of claim 12, further comprising soy milk.

16. A method of manufacturing a formulation comprising:
(a) combining a selected amount of a first component with a selected amount of a second component, wherein the first component is selected from the group consisting of jasmone, a jasmonate, jasmonic acid, oxo-phytodienoic acid and combinations thereof, and the second component comprises carnitine.

17. The method of claim 16, wherein the jasmonate includes methyl jasmonate.

18. The method of claim 16, wherein the second component further comprises an antioxidant, and the antioxidant comprises an isoflavone.

19. The method of claim 18, wherein the isoflavone includes at least one of genistein and daidzein.

20. The method of claim 16, wherein the method further comprises:
(b) combining the selected amounts of the first and second components in soy milk.

21. (Currently Amended) The method of claim 16, wherein the selected amount of the first component is at least about 100 micrograms, and the second component further comprises an antioxidant and includes at least about 20 milligrams of the antioxidant and at least about 3 grams of carnitine.

22. A formulation comprising soy milk and at least one of a jasmonate, jasmonic acid and oxo-phytodienoic acid.

* * * * *